United States Patent [19]
Hogg

[11] 3,963,983
[45] June 15, 1976

[54] PULSE AMPLITUDE DISCRIMINATING CIRCUIT

[75] Inventor: Walter R. Hogg, Miami Lakes, Fla.

[73] Assignee: Coulter Electronics, Inc., Hialeah, Fla.

[22] Filed: Oct. 16, 1973

[21] Appl. No.: 406,919

Related U.S. Application Data

[63] Continuation-in-part of Ser. No. 352,361, April 18, 1973, Pat. No. 3,810,011, which is a continuation-in-part of Ser. No. 40,231, May 25, 1970, Pat. No. 3,757,213.

[52] U.S. Cl. .................. 324/71 CP; 307/235 N; 328/116
[51] Int. Cl.$^2$ .................. G01N 27/00; H03K 5/20
[58] Field of Search ........ 324/71 CP, 103 P, 103 R; 235/92 PC; 328/115, 116; 307/235 N, 235 P

[56] References Cited
UNITED STATES PATENTS

| | | | |
|---|---|---|---|
| 3,221,253 | 11/1965 | Keyes | 324/103 P |
| 3,392,331 | 7/1968 | Coulter | 324/71 CP |
| 3,412,330 | 11/1968 | Klaver | 324/103 R |
| 3,670,150 | 6/1972 | Hogg et al. | 324/71 CP |
| 3,699,319 | 10/1972 | Berg | 324/71 CP |
| 3,701,029 | 10/1972 | Hogg | 324/71 CP |
| 3,783,247 | 1/1974 | Klein et al. | 324/71 CP |

Primary Examiner—R. V. Rolinec
Assistant Examiner—Ernest F. Karlsen
Attorney, Agent, or Firm—Silverman & Cass, Ltd.

[57] ABSTRACT

The pulse amplitude discriminating circuit is utilized in a system where particles in a fluid are caused to flow through a sensing zone and a particle pulse is generated for each particle sensed with the amplitude of each pulse being related to the size of the particle sensed. The discriminating circuit is operative to determine which pulses have an amplitude falling between predetermined upper and lower amplitude levels, for remembering each pulse while the determination is being made and for passing to a pulse analyzing circuit only the pulse heights of those remembered pulses which have an amplitude falling between the predetermined upper and lower amplitude levels. The pulse discriminating circuit includes first and second comparators for determining whether or not the particle pulse exceeds the lower and upper amplitude levels, a sample and hold circuit for remembering the pulse height of the particle pulse while the determination of pulse amplitude is being made, and control circuitry couple to the comparators and to an electronic switch between the output of the sample and hold circuit and the pulse analyzing circuit and operative to close the electronic switch when the output signal from the first comparator changes as a result of the trailing edge of the particle pulse is falling below the lower amplitude level with no change occurring in the output of the second comparator as the result of the amplitude of the particle pulse not exceeding the upper amplitude level.

12 Claims, 2 Drawing Figures

PULSE AMPLITUDE DISCRIMINATING CIRCUIT

CROSS REFERENCE TO RELATED APPLICATIONS

This application is a continuation in part of my earlier co-pending application Ser. No. 352,361 filed Apr. 18, 1973 now Pat. No. 3,810,011 issued May 7, 1974; which is a continuation in part of U.S. patent 3,757,213 filed on May 25, 1970 bearing Ser. No. 40,231 and issued on Sept. 4, 1973.

Both applications are assigned to the same assignee.

BACKGROUND AND SUMMARY OF THE INVENTION

The present invention relates to a pulse amplitude discriminating circuit. More specifically the invention relates to a discriminating circuit which remembers a pulse while a determination of the pulse height is made and then, if the pulse height falls within predetermined upper and lower levels the discriminating circuit, passes the pulse height of the remembered pulse to a pulse analyzing circuit.

Heretofore, various discriminating circuits have been proposed for use in particle analyzing devices for determining whether or not a particle pulse amplitude falls between upper and lower amplitude levels and for producing an output pulse if the particle pulse amplitude falls between the predetermined upper and lower levels. However, the previously proposed pulse discriminating circuits do not provide a memory means for remembering the pulse while a determination of pulse height is being made and for thereafter passing the pulse height to a pulse analyzing circuit. Examples of the previously proposed pulse amplitude discriminating circuits may be found in the following patents:

U.S. PATENT NUMBERS
3,127,505
3,259,842
3,271,671
3,331,950
3,392,331.

The discriminating circuit of the invention to be described in detail hereinafter, enables a technician to analyze the pulse heights of particles falling within predetermined upper and lower pulse height or amplitude levels and provides the technician with the pulse height of each pulse falling within the predetermined levels instead of merely providing pulses indicative of pulses falling within the predetermined levels. Such a circuit is especially useful in the measuring of the average volume of blood platelets which are the small particles in blood which are important in clotting. These platelets lie in the size range of approximately 3.5 to 35 cubic microns and are distinguishable from red cells by their small size. When making a platelet count, typically an attempt is made to separate the platelets from the red cells by centrifugation. However, this procedure is now wholly effective and is made doubly difficult by the fact that there are roughly 100 red cells for every platelet. Thus, a suspension of platelets is quite likely to have red cells in it. Accordingly, a pulse discriminating circuit of the type disclosed herein enables a technician to ignore pulses above a certain level such as those produced by red cells, while permitting the platelets to be counted and more particularly permitting a measurement of the average volume of blood platelets.

According to the invention there is provided in a system where particles in a fluid are caused to flow through a sensing zone and a particle pulse is generated for each particle sensed with the amplitude of each pulse being related to the size of the particle sensed, a pulse amplitude discriminating circuit for determining which pulses have an amplitude falling between predetermined upper and lower levels for remembering each pulse while the determination is being made and for passing to a pulse analyzing circuit only the pulse heights of those remembered pulses which have an amplitude falling between the predetermined upper and lower amplitude levels.

Also, according to the invention there is provided a method for analyzing particles in a fluid by causing the particles to flow through a sensing zone where a particle pulse is generated for each particle sensed and the amplitude of each particle pulse is related to the size of the particle sensed, the steps of determining which pulses have an amplitude falling between predetermined upper and lower amplitude levels, remembering each pulse while said determination is being made, and passing to a pulse analyzing circuit only the pulse heights of those remembered pulses which have an amplitude falling between the predetermined upper and lower amplitude levels.

DESCRIPTION OF THE PREFERRED EMBODIMENT

Figure 1:
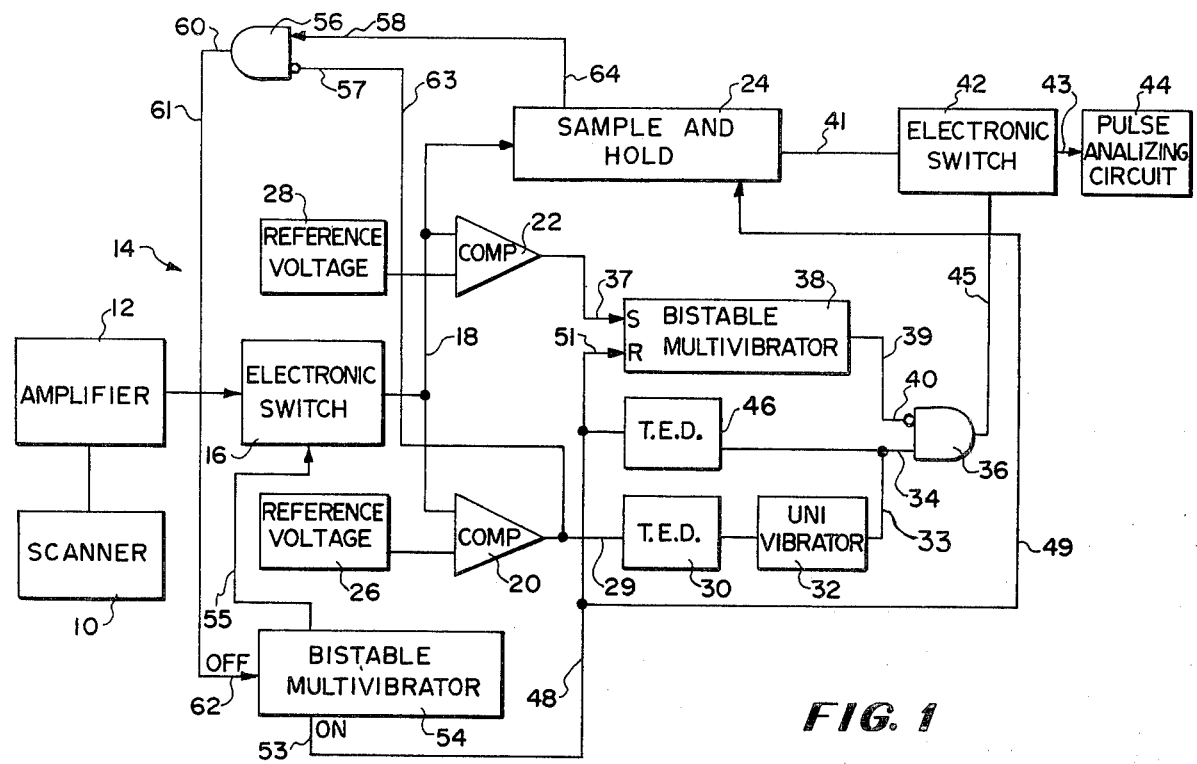
FIG. 1 is a schematic block diagram of the pulse amplitude discriminating circuit of the invention.

Referring to FIG. 1 there is shown schematically a scanner 10 and an amplifier 12 of a particle pulse generating circuit associated with a sensing zone in a particle analyzing device. Such a scanner 10 and amplifier 12 can be of the type disclosed in U.S. Pat. No. 3,259,842, the disclosure of which is incorporated herein by reference. The output of the amplifier 12 is applied to the pulse amplitude discriminating circuit, or simply, electric circuit, of the invention generally identified by the reference numeral 14.

As shown, the electric circuit 14 includes an electronic switch 16 to which the output of the amplifier 12 is applied. The other side of the electronic switch 16 is connected to a conductor 18 which serves as a bus for supplying the particle pulse simultaneously to a first comparator 20, a second comparator 22 and a sample and hold circuit 24. As shown, a first reference voltage 26 is applied to one input of the first comparator 20 and the bus 18 is connected to a second input of the comparator 20. Likewise, a second reference voltage 28 is applied to a first input of the second comparator 22 and the bus 18 is connected to the second input of the second comparator 22.

The output of the comparator 20 is connected via conductor 29 to a trailing edge detector 30 which in turn is connected to a univibrator 32 the output of which is connected via conductor 33 to a first input 34 of an AND circuit 36. The output of the second comparator 22 is connected to a set input 37 of a bistable multivibrator 38 the output of which is connected via conductor 39 to an inverted input 40 of the AND circuit 36. In the illustrated embodiment, the bistable multivibrator is preferably an R.S. flip-flop.

The output of the sample and hold circuit 24 is connected via a conductor 41 to an electronic switch 42 the other side of which is connected via a conductor 43 to a pulse analyzing circuit 44. As shown, the output of the AND circuit 36 is connected via a conductor 45 to the gate input of the electronic switch 42. The pulse analyzing circuit 44 can include various subcircuits commonly utilized in analyzing pulses. In particular, the circuit 44 will include circuitry for averaging the pulse heights and for obtaining a signal indicative of mean particle volume. Such circuitry for providing a readout of mean particle volume can be of the type disclosed in U.S. Pat. No. 3,473,010 the disclosure of which is incorporated herein by reference. The pulse analyzing circuit can also include circuits for totalizing the pulse heights to obtain an indication of total particle volume, circuits for counting the pulses received and other circuits which are well known in the art of particle analysis.

The trailing edge detector 30, univibrator 32, the AND circuit 36 and the flip-flop 38 can be considered as control circuitry for the electric circuit 14. This control circuitry preferably also includes a trailing edge detector 46 which is connected to the conductor 33 and which has an output connected to a conductor 48. The conductor 48 applies the pulse or signal out of the trailing edge detector 46 to the sample and hold circuit 24 via a conductor 49 for clearing the sample and hold circuit 24. The conductor 48 is also connected to the reset input 51 of the flip-flop 38. The conductor 48 is also connected to an on, or set input 53 of a second bistable multivibrator 54 which is also preferably an R.S. flip-flop. The output of the flip-flop 54 is connected via a conductor 55 to the electronic switch 16.

The electric circuit 14 includes additional control circuitry which also can be considered as part of the overall control circuitry in the electric circuit 14. This additional control circuitry includes a second AND circuit 56 which has a first, inverted input 57, a second input 58 and an output 60. The output 60 is connected via a conductor 61 to the off or reset input 62 of the bistable multivibrator 54. As shown, the output of the first comparator 20 is connected via a conductor 63 to the first input 57 of the second AND circuit 56. Also, an output terminal in the sample and hold circuit 24 is connected via a conductor 64 to the second input 58 of the second AND circuit 56.

Figure 2:
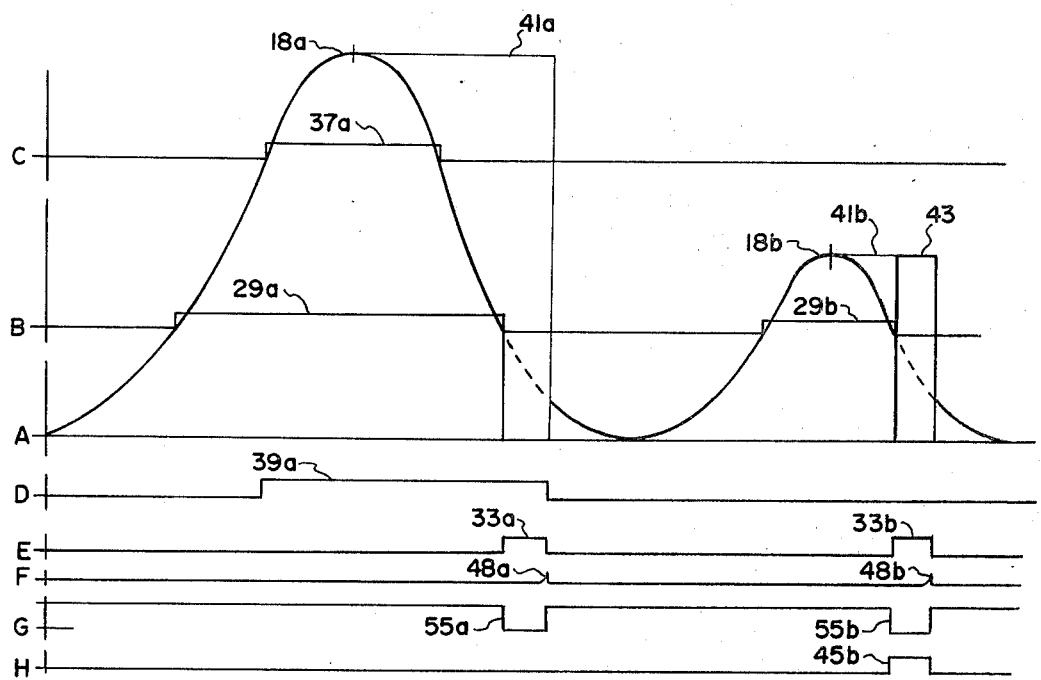
FIG. 2 is a diagram consisting of a series of graphs all on the same time scale illustrating various wave shapes of signals of pulses at different points in the pulse amplitude discriminating circuit shown in FIG. 1.

The operation of the pulse amplitude discriminating circuit, or electric circuit, 14 will now be described with reference to FIG. 2. In the following description each of the various pulses will be identified by the reference numeral for the conductor on which it appears and by a lower case letter a or b. Letter a relates to a particle pulse which has a peak amplitude greater than the second reference voltage 28, and letter b relates to a particle pulse which has a peak amplitude which falls between the levels established by the reference voltages 26 and 28. Briefly, with reference to FIG. 2 graph A shows the signals appearing on conductor 18, the conductor 41 and the conductor 43. Superimposed on graph A is graph B, the base line of which is at a height above the base line of graph A equal to the first reference voltage 26. Graph B shows the signal which appears on conductor 29. Graph C is also superimposed on graph A has a base line at a height above the base line of graph A equal to the reference voltage 28 and shows the signal appearing on the input 37 of flip-flop 38.

Graph D shows the signal appearing on conductor 39, graph E shows the signal appearing on conductor 33, graph F shows the signal appearing on conductor 48, graph G shows the signal appearing on conductor 55, and graph H shows the signal appearing on conductor 45.

In the operation of the electric circuit 14 a particle pulse is passed through the electronic switch 16 and the resulting signal is identified by the reference numeral 18a in graph A. As the amplitude of the signal or pulse 18a increases it reaches the level of the reference voltage 26 causing an output signal 29a (graph B) to appear at the output of the first comparator 20. As the particle pulse 18a increases in amplitude it reaches the level of the second reference voltage 28 and causes the comparator 22 to produce an output signal 37a (graph C). The output signal 37a operates the flip-flop 38 to cause same to produce an output signal 39a (graph D) which is applied via inverted input 40 to the AND circuit 36. As a result the input 40 of the AND circuit 36 receives a logic 0 signal. When the pulse 18a decreases below the first reference voltage 26, the signal 29a goes from a logic 1 to a logic 0, and the trailing edge of pulse 29a triggers the trailing edge detector 30 to produce a pulse which operates the univibrator 32. The univibrator 32 then produces a logic 1 signal 33a, shown in graph E. This logic 1 signal is applied to the input 34 of the AND circuit 36. At this point in time there is a logic 0 and a logic 1 input to the AND circuit 36 preventing the AND circuit 36 from producing an output signal on the conductor 45 to operate the switch 42. As a result, the height of signal 41a (graph A) on conductor 41 is not passed through the electronic switch 42 to the pulse analyzing circuit 44.

At the time the amplitude of the pulse 18a falls below the second reference voltage 26, thus terminating the signal 29a, the change from a logic 1 to a logic 0 on conductor 29 and 63 is applied to the inverted input 57 of the AND circuit 56 and inverted to a logic 1 signal. At the same time the sample and hold circuit 24 has saturated at the peak of pulse 18a and a logic 1 signal is applied via the conductor 64 to the other input 58 of the second AND circuit 56. An output pulse is then generated by the AND circuit 56 and applied via the conductor 61 to the off or reset input 62 of the flip-flop 54 which then produces a signal 55a (graph G) which turns off the electronic switch 16 to prevent further particle pulses from being applied to the sample and hold circuit 24 until the sample and hold circuit 24 is cleared. Turning off of the switch 16 causes the signal 18a on the conductor 18 to go to 0 as shown in graph A.

In the meantime, the univibrator 32 is producing the pulse on signal 33a for a predetermined short duration. At the termination of the pulse 33a the trailing edge thereof is detected by the trailing edge detector 46 and generates a short signal 48a (graph F) which is applied via the conductors 48 to the flip-flop 54 which then turns on the switch 16 for receiving another pulse. At the same time, the signal 48a is applied to the reset input 51 of the flip-flop 38 to reset same causing the signal 39a to go from logic 1 to logic 0. Additionally, the pulse 48a is applied via conductor 48 and 49 to the sample and hold circuit 24 to clear the same of the signal 41a.

When a subsequent signal 18b is applied to the conductor 18 a signal 29b similar to the signal 29a is generated at the output of the comparator 20 so long as the pulse 18b exceeds the reference voltage 26 as represented by the height of the base line of graph B above the base line of graph A. Since the amplitude of the pulse 18b does not reach the reference voltage 28 as represented by the base line of the graph C, the output of the second comparator 22 does not change from a logic 0 to logic 1. As a result the flip-flop 38 is not activated and the output signal remains at logic 0 as shown in graph D. This logic 0 is inverted at the inverted input 40 of the AND circuit 36 to apply a logic 1 to the AND circuit 36. Then, when the amplitude of the pulse 18b falls below the reference voltage 26 represented by the base line of graph B, the univibrator 32 produces the pulse 33b which is applied to the AND circuit 36. The AND circuit 36, now receiving two logic 1 inputs, produces a logic 1 output 45b on the conductor 45 which is applied to the electronic switch 42 for a short period of time equal to the duration of the pulse 33b as shown in graphs H and E. During this time period that the electronic switch 42 is closed the pulse height stored in the sample and hold circuit 24 is transmitted via the conductor 43 to the pulse analyzing circuit. This signal on conductor 43 will have a pulse height equal to the pulse height on line 41b and a duration equal to the duration of the univibrator 33 as shown at 43b in graph A.

It will be understood from the foregoing description that for all particle pulses having an amplitude falling between the reference voltages 26 and 28 an output pulse is applied via the conductor 43 to the pulse analyzing circuit 44. Each of these output pulses will have a pulse height or amplitude equal to the peak amplitude of the particle pulse and a duration equal to the duration of the pulses from the one short or univibrator 32. Also, at the end of the pulse 33b the trailing edge detector 46 is again triggered to produce a pulse 48b (graph F) which resets the sample and hold circuit 24, the flip-flop 38 and the flip-flop 54 in the manner described above.

The pulse amplitude discriminating circuit 14 of the present invention provides a number of advantages, some of which have been described above, and others of which are inherent in the invention. Also, various modifications and variations can be made to the circuit 14 without departing from the spirit or scope of the invention. In this respect, it is to be understood that the sample and hold circuit 24 is but one form of memory means which can be utilized in the circuit 14. Thus, a delay line or other type of memory means could be utilized in place of the sample and hold circuit 24. Also, other modifications will occur to those skilled in the art. Accordingly, the scope of the invention is only to be limited as necessitated by the accompanying claims.

I claim:

1. In a system where particles in a fluid are caused to flow through a sensing zone and a particle pulse is generated for each particle sensed with the amplitude of each pulse being related to the size of the particle sensed, the improvement comprising electric circuit means for determining which pulses having an amplitude falling between predetermined upper and lower amplitude levels, for remembering each pulse while said determination is being made and for passing to a pulse analyzing circuit only the pulse heights of those remembered pulses which have an amplitude falling between the predetermined upper and lower amplitude levels.

2. The system according to claim 1 wherein said electric circuit means includes a first comparator having a first input for receiving the particle pulse and a second input connected to a first reference voltage establishing the lower amplitude level, a second comparator having a first input for receiving the particle pulse and a second input connected to a second reference voltage for establishing the upper amplitude level, a sample and hold circuit having an input for receiving the particle pulse, an electronic switch connected to the output of the sample and hold circuit, and control circuit means coupled to the outputs of said first and second comparators and to said electronic switch for closing said electronic switch when the output signal from said first comparator changes as a result of the trailing edge of the particle pulse falling below the first reference voltage with no change occurring in the output of the second comparator as a result of the amplitude of the particle pulse not exceeding the second reference voltage applied to the second comparator.

3. The system according to claim 2 wherein said contol circuit means includes an AND circuit having an output connected to said electronic switch and first and second inputs, a trailing edge detector and a univibrator connected in series between the output of said first comparator and said first input of said AND circuit and bistable means connected between the output of said second comparator and said second input of said AND circuit for preventing an output signal from being applied by said AND circuit to said electronic switch when said bistable means receives a signal from said second comparator as a result of the amplitude of the particle pulse exceeding said second reference voltage applied to said second comparator.

4. The system according to claim 3 wherein said control means includes a second trailing edge detector connected to the output of said univibrator, the output of said second trailing edge detector being connected to said bistable means for resetting the same and connected to said sample and hold circuit for clearing the pulse height held therein.

5. The system according to claim 4 including circuitry associated with said sensing zone for generating said particle pulses, a second electronic switch connected between said circuitry and the inputs to said comparators and to said sample and hold circuit, a second bistable means connected to said second electronic switch for controlling same, a second AND circuit having an output connected to said second bistable means and first and second inputs, the output of said first comparator being connected to said first input of said second AND circuit and an output of said sample hold circuit being connected to said second input of said AND circuit, so that when a signal from said first comparator generated as a result of the particle pulse falling below the first reference voltage is applied to said first input of said second AND circuit while said second input of said second AND circuit is receiving a signal from said sample and hold circuit as a result of the particle pulse applied thereto having reached its peak amplitude, an output signal from said second AND circuit is applied to said second bistable means for causing same to turn off said second electronic switch and thereby prevent said electric circuit means from receiving a subsequent particle pulse until said sample and hold circuit is cleared of the pulse height stored therein, and said second trailing edge detector is operable to send a "turn on" signal to said second bistable means to turn on said second electronic switch at the same time it is applying a signal to said sample and hold circuit for clearing same.

6. The system according to claim 2 including an electronic switch connected between circuitry associated with said sensing zone for generating said particle pulses and the inputs to said first and second comparators and said sample and hold circuit, bistable means connected to said electronic switch for controlling operation of same, and an AND circuit having an output connected to said bistable means and first and second inputs, the output of said first comparator being connected to said first input and an output of said sample and hold circuit being connected to said second input such that when a signal is applied from said first comparator to said first input as a result of the particle pulse falling below the first reference voltage while a signal is being applied to said second input of said AND circuit as the result of the particle pulse applied to said sample and hold circuit having reached its peak amplitude, an output signal from said AND circuit is applied to said bistable means for opening said electronic switch.

7. The system according to claim 1 including a pulse analyzing circuit which includes means for averaging the pulse heights applied thereto and for producing an output signal which is indicative of mean particle volume.

8. In a method for analyzing particles in a fluid by causing the particles to flow through a sensing zone where a particle pulse is generated for each particle sensed and the amplitude of each particle pulse is related to the size of the particle sensed, the improvement comprising the steps of determining which pulses have an amplitude falling between predetermined upper and lower amplitude levels, remembering each pulse while said determination is being made, and passing to a pulse analyzing circuit only the pulse heights of those remembered pulses which have an amplitude falling between the predetermined upper and lower amplitude levels.

9. The method according to claim 8 wherein said steps of determining pulse amplitude and simultaneously remembering each pulse is accomplished by comparing the changing pulse amplitude with a first reference voltage related to the lower amplitude level and a second reference voltage related to the upper amplitude level while simultaneously sampling the particle pulse and holding the peak amplitude of the particle pulse.

10. The method according to claim 9 wherein said sampling and holding is accomplished by applying the particle pulse to a sample and hold circuit and said step of passing only those pulse heights of remembered pulses which have an amplitude falling between the predetermined upper and lower amplitude levels is accomplished by generating a signal when the changing amplitude of the particle pulse exceeds the reference voltages associated with the upper and lower amplitude levels and passing the pulse height stored in the sample and hold circuit when only one signal is established as a result of the amplitude of the particle pulse exceeding only the reference voltage related to the lower amplitude level.

11. The method according to claim 10 including the step of clearing the sample and hold circuit after a determination of the pulse amplitude has been made.

12. The method according to claim 11 including the step of terminating the application of the particle pulse to the sample and hold circuit after a determination of the pulse amplitude has been made and, where the pulse amplitude falls between the upper and lower amplitude levels, after the pulse height has been passed to the pulse analyzing circuit and until the sample and hold circuit is cleared.

* * * * *